United States Patent
Huang et al.

(10) Patent No.: US 10,485,453 B2
(45) Date of Patent: Nov. 26, 2019

(54) STRETCH SENSOR WITH ELASTIC DIELECTRIC LAYER

(71) Applicant: TAIWAN ALPHA ELECTRONIC CO., LTD., Taoyuan (TW)

(72) Inventors: Tzu-Hsuan Huang, Taoyuan (TW); Wei-Liang Liu, Taoyuan (TW)

(73) Assignee: TAIWAN ALPHA ELECTRONIC CO., LTD., Taoyuan (TW)

( * ) Notice: Subject to any disclaimer, the term of this patent is extended or adjusted under 35 U.S.C. 154(b) by 82 days.

(21) Appl. No.: 15/858,664

(22) Filed: Dec. 29, 2017

(65) Prior Publication Data

US 2018/0184949 A1 Jul. 5, 2018

(30) Foreign Application Priority Data

Dec. 29, 2016 (TW) .............................. 105143777 A
Dec. 15, 2017 (TW) .............................. 106144230 A

(51) Int. Cl.
*G01R 27/26* (2006.01)
*A61B 5/11* (2006.01)
(Continued)

(52) U.S. Cl.
CPC .......... *A61B 5/1126* (2013.01); *A61B 5/6801* (2013.01); *G01B 7/16* (2013.01);
(Continued)

(58) Field of Classification Search
CPC ............ A61B 2562/164; A61B 5/1126; A61B 5/1116; A61B 5/6802; A61B 5/1112; A61B 5/1121; A61B 5/1075; A61B 5/1114; A61B 5/1123; A61B 5/1127; A61B 5/4848; A61B 5/6801; G01B 7/22; G01B 7/16; G01B 7/18; G01B 1/00; G01B 7/044; G01B 7/08; G01L 1/146; G01L 1/16; G01L 1/142; G01L 1/148; G01L 1/005; G01L 1/14; G01L 1/20; G01N 27/226; G01N 27/22; G01N 27/227; G01N 27/4071;
(Continued)

(56) References Cited

U.S. PATENT DOCUMENTS 10,274,305 B2 * 4/2019 Huang ..................... G01B 7/22
2014/0090489 A1 * 4/2014 Taylor ....................... G01L 1/00
73/862.626

(Continued)

*Primary Examiner* — Vinh P Nguyen
(74) *Attorney, Agent, or Firm* — Muncy, Geissler, Olds & Lowe, P.C.

(57) ABSTRACT

A stretch sensor includes a first elastic insulating layer, a first elastic conductive layer, an elastic dielectric layer, a second elastic conductive layer and a second elastic insulating layer sequentially piled together thereon. The first and the second elastic insulating layers include the same elastic resin, and the first and the second elastic conductive layer include the same elastic resin and the same conductive material. The elastic dielectric layer includes the elastic resin and a dielectric material, in which the dielectric material comprises at least one of an $Sr_{1-x}Ca_xTiO_3$ compound, an $Sr_{1-y}Ba_yTiO_3$ compound, and a $BaTiO_3$ compound so as to make the dielectric constant of the dielectric material within 15.65-2087.3 F/m.

12 Claims, 9 Drawing Sheets

(51) Int. Cl.
*A61B 5/00* (2006.01)
*G01L 1/14* (2006.01)
*G01N 27/22* (2006.01)
*G01B 7/16* (2006.01)
*G01D 5/241* (2006.01)

(52) U.S. Cl.
CPC .............. *G01D 5/241* (2013.01); *G01L 1/146* (2013.01); *G01N 27/226* (2013.01); *A61B 2562/0261* (2013.01)

(58) Field of Classification Search
CPC ...... G01N 33/5438; G01D 5/24; G01D 5/241; G01C 2009/182; G01R 27/26; G01R 27/2605; G01R 27/2617
See application file for complete search history.

(56) References Cited

U.S. PATENT DOCUMENTS

| | | | |
|---|---|---|---|
| 2016/0033343 A1* | 2/2016 | Park | G01L 1/205 73/862.046 |
| 2016/0238368 A1* | 8/2016 | O'Brien et al. | B32B 7/05 |
| 2016/0302729 A1* | 10/2016 | Starr | A61B 5/0004 |

* cited by examiner

STRETCH SENSOR WITH ELASTIC DIELECTRIC LAYER

This application claims the benefit of Taiwan Patent Application Serial No. 105143777, filed Dec. 29, 2016 and Ser. No. 106144230, filed Dec. 15, 2017, the subject matter of which is incorporated herein by reference.

BACKGROUND OF THE INVENTION

1. Field of the Invention

The invention relates to a stretch sensor, and more particularly to the stretch sensor that has an elastic dielectric layer produced from an elastic resin and a dielectric material.

2. Description of the Prior Art

In the field of human-machine or human-computer interaction, a wearable device is worn onto a user so as largely to become part of the user for being operated in coherence with the human body. Hence, the wearable device can be effectively and smoothly introduced into people's daily life. Also, the convenience provided by the wearable device can benefit people a better life.

Nevertheless, since the wearable device applies various sensors to detect user's motions, thus flexibility and elasticity are basic requirements for the sensors. Thereupon, versatile movements on a soft human body can thus be detected.

Currently, in order to equip the sensor with elasticity, an elastic resin is introduced to form an elastic dielectric layer, and the electrodes are disposed to two opposing sides of the elastic dielectric layer, such that an induced capacitor having the electrodes is formed across the elastic dielectric layer. In the case that the elastic dielectric layer is stretched so as to reduce the spacing between the electrode, then the capacitance of induction capacitor would be varied. By analyzing the capacitance change of the induction capacitor, the tensile strain as well as the corresponding tensile deformation can be understood. However, since the elastic resin has a lower K value (for example, the rubber has a dielectric constant of about 2-3), thus the elastic dielectric layer made of a rubber can only provide limited induction capacitance. It is the reason why the sensor having the elastic dielectric layer made of an elastic resin such as a rubber can't serve as a stretch sensor that detects the tensile deformation by realizing a variation in reduction capacitance.

In addition, in the current art, though a material modification can be applied to the elastic resin so as to enhance its polarized ability and thus to increase the dielectric constant, yet such a resort would increase significantly the entire manufacturing cost.

SUMMARY OF THE INVENTION

In view of the prior art, the majority of current stretch sensors apply the elastic resin as the elastic dielectric layer. However, since the elastic resin generally has a lower dielectric constant, the capacitor having the elastic dielectric layer can only contribute limited capacitance, and thereby the sensitivity in detecting a stretching rate would be poor. Though a material modification upon the elastic resin can be applied to increase the dielectric constant, yet the entire cost hike would be hard to be accepted. Accordingly, it is an object of the present invention to provide a stretch sensor that increases an equivalent dielectric constant of the elastic dielectric layer by adding a dielectric material.

In the present invention, the stretch sensor includes a first elastic insulating layer, a first elastic conductive layer, an elastic dielectric layer, a second elastic conductive layer and a second elastic insulating layer. The first elastic insulating layer includes an elastic resin. The first elastic conductive layer, disposed on the first elastic insulating layer, includes the elastic resin and a conductive material. The elastic dielectric layer, disposed on the first elastic conductive layer, includes the elastic resin and a dielectric material, the dielectric material being composed by at least one of an $Sr_{1-x}Ca_xTiO_3$ compound, an $Sr_{1-y}Ba_yTiO_3$ compound and a $BaTiO_3$ compound with $0.1 \leq x \leq 0.9$ and $0.1 \leq y \leq 0.9$, so as to have a dielectric constant (K value) of the dielectric material within 5.65-2087.3 F/m. The second elastic conductive layer, disposed on the elastic dielectric layer, includes the elastic resin and the conductive material. The second elastic insulating layer, disposed on the second elastic conductive layer, includes the elastic resin. Thereupon, the dielectric constant of the elastic dielectric layer is within 4.85-408.31 F/m.

In the present invention, constituents of the elastic resin includes at least a mono vinyl terminated polydimethylsiloxane, a vinyl modified Q silica resin and a polydimethylhydrogensiloxane (Methylhydrosiloxane-dimethylsiloxane copolymer, trimethylsiloxane terminated).

In addition, a content of the mono vinyl terminated polydimethylsiloxane in the elastic resin is larger than 70 wt %, a content of the vinyl modified Q silica resin in the elastic resin is less than 30 wt %, and a content of the polydimethylhydrogensiloxane in the elastic resin is less than 10 wt %.

In one embodiment of the present invention, the elastic dielectric layer includes 10-20 wt % the dielectric material, and the dielectric material including the $Sr_{1-x}Ca_xTiO_3$ compound has the dielectric constant within 15.65-31.31 F/m so as to have the dielectric constant of the elastic dielectric layer within 4.85-9.45 F/m.

In one embodiment of the present invention, the elastic dielectric layer includes 10-20 wt % the dielectric material, and the dielectric material including the $Sr_{1-y}BayTiO_3$ compound has the dielectric constant within 139.84-206.64 F/m so as to have the dielectric constant of the elastic dielectric layer within 18.66-44.63 F/m.

In one embodiment of the present invention, the elastic dielectric layer includes 10-20 wt % the dielectric material, and the dielectric material including the $BaTiO_3$ compound has the dielectric constant of 2087.3 F/m so as to have the dielectric constant of the elastic dielectric layer within 207.48-408.31 F/m.

As described above, since the stretch sensor provided by the present invention adopts the elastic dielectric layer composed of the elastic resin and the dielectric material, thus the equivalent dielectric constant of the elastic dielectric layer can be adjusted by varying the addition of the dielectric material according to user's needs.

All these objects are achieved by the stretch sensor described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to a stretch sensor. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
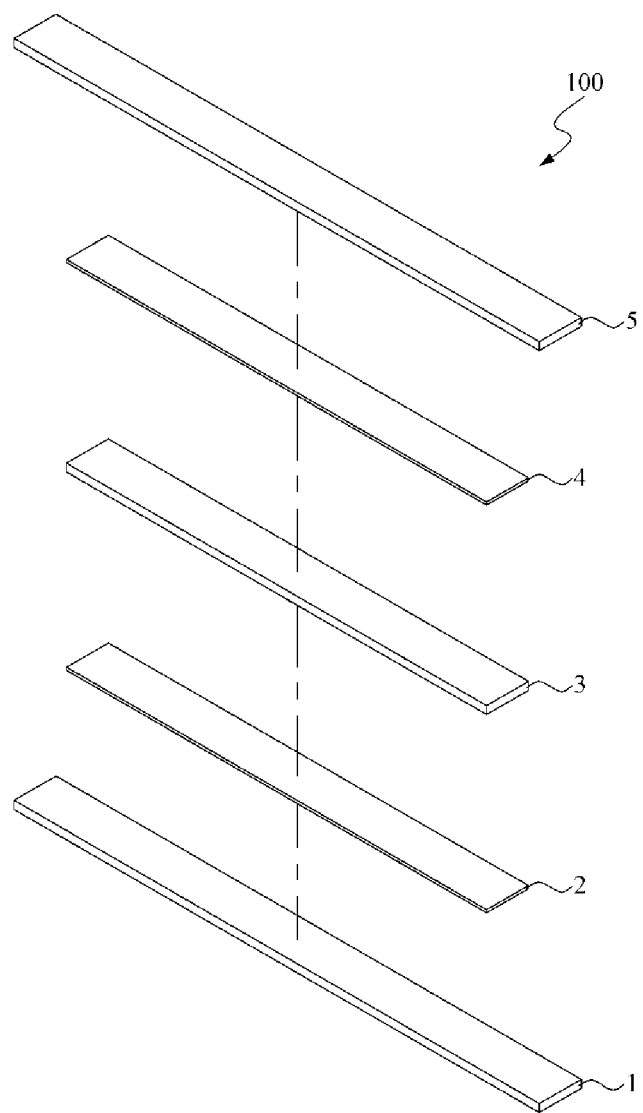
FIG. 1 is a schematic exploded view of a preferred embodiment of the stretch sensor in accordance with the present invention.
Figure 2:
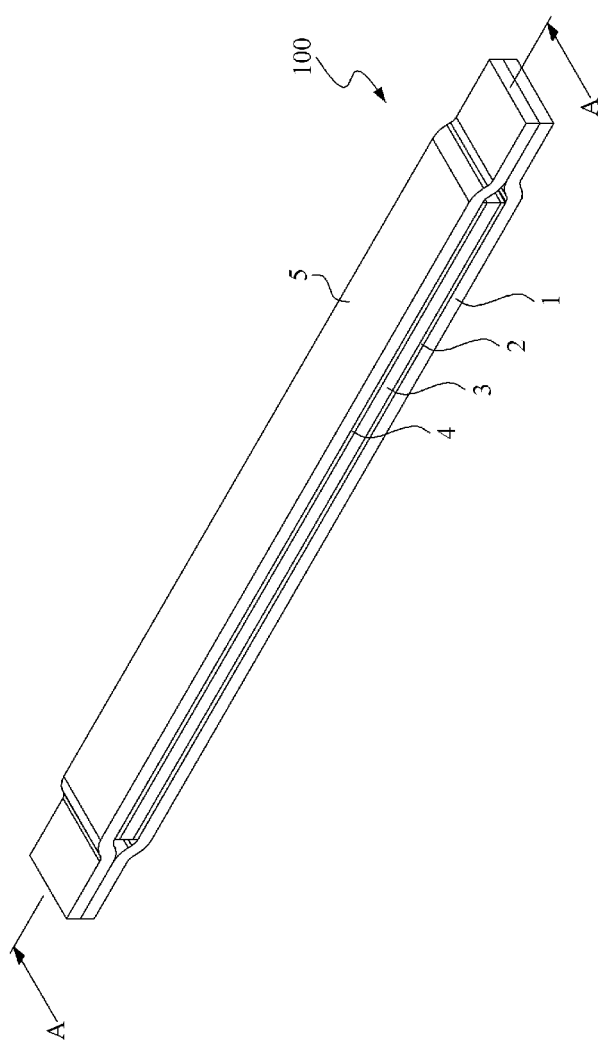
FIG. 2 is a schematic perspective view of FIG. 1.

Refer now to FIG. 1 and FIG. 2; where FIG. 1 is a schematic exploded view of a preferred embodiment of the stretch sensor in accordance with the present invention, and FIG. 2 is a schematic perspective view of FIG. 1.

As shown, the stretch sensor 100 includes a first elastic insulating layer 1, a first elastic conductive layer 2, an elastic dielectric layer 3, a second elastic conductive layer 4 and a second elastic insulating layer 5.

The first elastic insulating layer 1 includes a elastic resin, where constituents of the elastic resin include a mono vinyl terminated polydimethylsiloxane (CAS No. 68951-99-5), a vinyl modified Q silica resin (CAS No. 68584-83-8) and a polydimethylhydrogensiloxane (Methylhydrosiloxane-dimethylsiloxane copolymer, trimethylsiloxane terminated, CAS No. 68037-59-2). The content of the mono vinyl terminated polydimethylsiloxane in the elastic resin is larger than 70 wt %, the content of the vinyl modified Q silica resin in the elastic resin is less than 30 wt %, and the content of the polydimethylhydrogensiloxane in the elastic resin is less than 10 wt %. In this preferred embodiment, the elastic resin includes 75 wt % mono vinyl terminated polydimethylsiloxane, 20 wt % vinyl modified Q silica resin and 5 wt % polydimethylhydrogensiloxane, and the first elastic insulating layer 1 can have a stretching rate up to above 340%.

As described above, in practice, a cross-linking degree of the elastic resin can be raised by adding a cross-linking agent or by radiation of electronic beams, such that elasticity and strength of the elastic resin can be enhanced. In the present invention, the cross-linking agent can be, but not limited to, a dicumyl peroxide (DCP).

The first elastic conductive layer 2 is disposed on the first elastic insulating layer 1, and constituents of the first elastic conductive layer 2 includes the aforesaid elastic resin and a conductive material, where the conductive material can be nano carbon tubes, nano silver fibers or the like. Preferably, a content of the conductive material in the first elastic conductive layer 2 is about 50 wt %.

The elastic dielectric layer 3, disposed on the first elastic conductive layer 2, includes the aforesaid elastic resin and a dielectric material, where the dielectric material can be an $Sr_{1-x}Ca_xTiO_3$ compound with $0.1 \leq x \leq 0.9$ so as to have the dielectric constant (K value) of the elastic dielectric layer 3 within 15.65 F/m and 31.31 F/m.

Table 1 as follows lists the dielectric constants of the elastic dielectric layer 3 with different contents of the dielectric material. As shown, at x=0.1, the dielectric material of $Sr_{0.9}Ca_{0.1}TiO_3$ compound has a dielectric constant of 31.31 F/m; and, at x=0.9, the dielectric material of $Sr_{0.1}Ca_{0.9}TiO_3$ compound has a dielectric constant of 15.65 F/m. In addition, since the content of the dielectric material varies from 10 wt % to 20 wt %, thus, at different x values for the dielectric material ($Sr_{1-x}Ca_xTiO_3$ compound), the dielectric constant of the dielectric material would be different. As listed in Table 1, the dielectric constant of the elastic dielectric layer 3 varies from 4.85 F/m to 9.45 F/m, as the content of the dielectric material in the elastic dielectric layer 3 varies from 10 wt % to 20 wt %.

TABLE 1

| Dielectric material | Dielectric constant (F/m) | Content of dielectric material | Dielectric constant of elastic dielectric layer |
|---|---|---|---|
| $Sr_{0.9}Ca_{0.1}TiO_3$ compound | 31.31 | 10 wt % | 6.45 |
| $Sr_{0.1}Ca_{0.9}TiO_3$ compound | 15.65 | 10 wt % | 4.85 |
| $Sr_{0.9}Ca_{0.1}TiO_3$ compound | 31.31 | 20 wt % | 9.45 |
| $Sr_{0.1}Ca_{0.9}TiO_3$ compound | 15.65 | 20 wt % | 6.25 |

In this embodiment, except for the aforesaid $Sr_{1-x}Ca_xTiO_3$ compound, the dielectric material can be an $Sr_{1-y}Ba_yTiO_3$ compound or a BaTiO3 compound, in which $0.1 \leq y \leq 0.9$. By adding 10-20 wt % of the $Sr_{1-y}Ba_yTiO_3$ compound or the $BaTiO_3$ compound to the elastic dielectric layer 3, the variations of the dielectric constant of the elastic dielectric layer 3 are listed in Table 2 and Table 3, respectively.

TABLE 2

| Dielectric material | Dielectric constant (F/m) | Content of dielectric material | Dielectric constant of elastic dielectric layer |
|---|---|---|---|
| $Sr_{0.9}Ba_{0.1}TiO_3$ compound | 206.64 | 10 wt % | 24.63 |
| $Sr_{0.1}Ba_{0.9}TiO_3$ compound | 139.84 | 10 wt % | 18.66 |
| $Sr_{0.9}Ba_{0.1}TiO_3$ compound | 206.64 | 20 wt % | 44.63 |
| $Sr_{0.1}Ba_{0.9}TiO_3$ compound | 139.84 | 20 wt % | 32.65 |

TABLE 3

| Dielectric material | Dielectric constant (F/m) | Content of dielectric material | Dielectric constant of elastic dielectric layer |
|---|---|---|---|
| BaTiO$_3$ compound | 2087.3 | 10 wt % | 207.48 |
| BaTiO$_3$ compound | 2087.3 | 20 wt % | 408.31 |

As shown in Table 1, Table 2 and Table 3, it is proved that, in the present invention, the dielectric constant of the elastic dielectric layer 3 can vary within 4.85 F/m to 408.31 F/m by adding 10-20 wt % dielectric material, where the dielectric material includes at least one of the $Sr_{1-x}Ca_xTiO_3$ compound, the $Sr_{1-y}Ba_yTiO_3$ compound and the $BaTiO_3$ compound.

In this embodiment, constituents of the second elastic conductive layer 4 are the same as those of the first elastic conductive layer 2, which include the elastic resin and the conductive material. Thus, details thereabout are omitted herein.

Further, in this embodiment, the second elastic insulating layer 5 is identical to the first elastic insulating layer 1, both including the same elastic resin. Thus, details thereabout are omitted herein.

Figure 3:
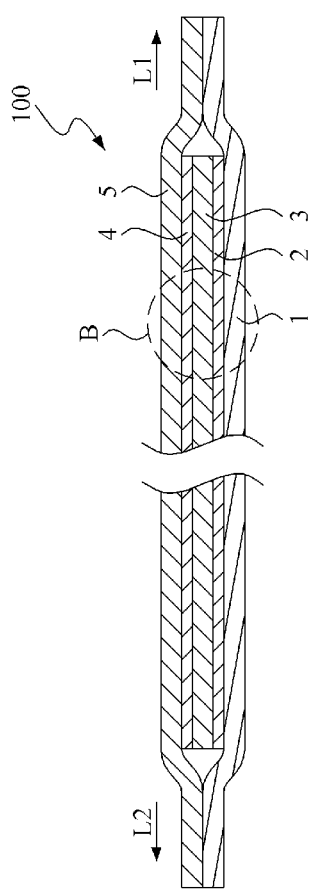
FIG. 3 is a schematic cross-sectional view of FIG. 2 along line A-A.
Figure 4:
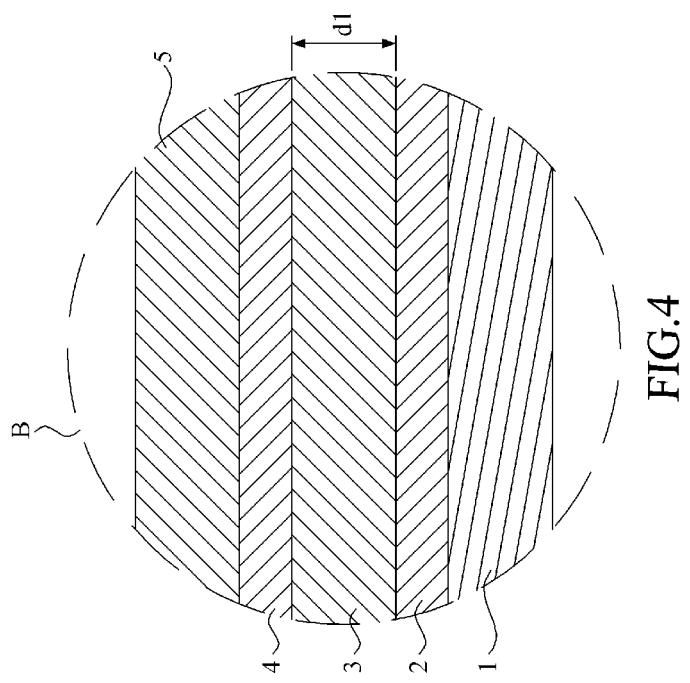
FIG. 4 is an enlarged view of area B of FIG. 3.
Figure 5:
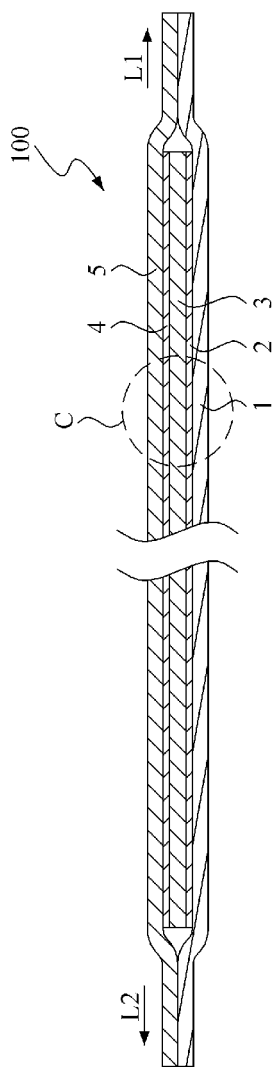
FIG. 5 shows another state of FIG. 3, where the stretch sensor has been stretched.
Figure 6:
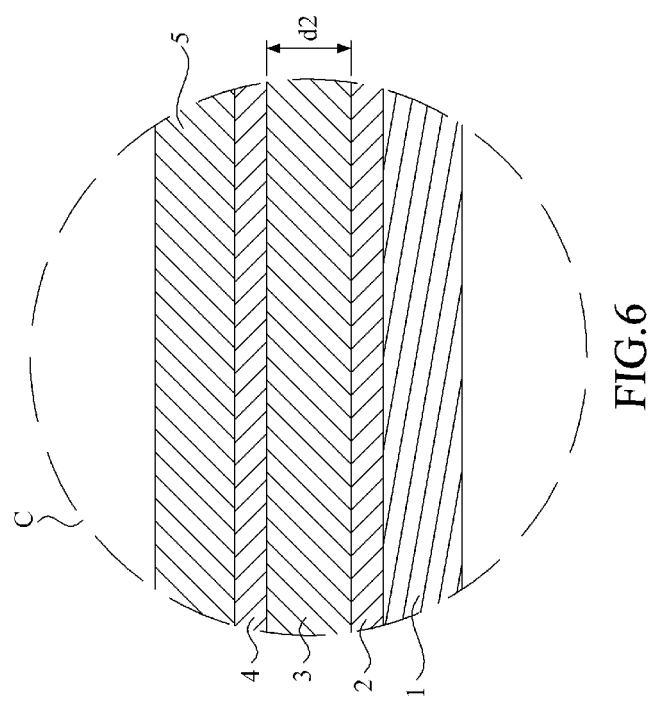
FIG. 6 is an enlarged view of area C of FIG. 5.

Refer now to FIG. 3 to FIG. 6; where FIG. 3 is a schematic cross-sectional view of FIG. 2 along line A-A, FIG. 4 is an enlarged view of area B of FIG. 3, FIG. 5 shows another state of FIG. 3, where the stretch sensor has been stretched, and FIG. 6 is an enlarged view of area C of FIG. 5.

As shown, while the stretch sensor 100 is stretched with opposing ends thereof extending in a first direction L1 and a second direction L2 reversely to the first direction L1, respectively, the thickness of the elastic dielectric layer 3 would be reduced from a first thickness d1 to a second thickness d2.

As described above, according to C=εA/d (C is the capacitance, ε is the capacitance rate of medium, A is the effective area of the two parallel conductive plates, and d is the spacing between the two parallel conductive plates), while the thickness of the elastic dielectric layer 3 is reduced from the first thickness d1 to the second thickness d2, the capacitance between the first elastic conductive layer 2 and the second elastic conductive layer 4 would be respectively increased.

Figure 7:
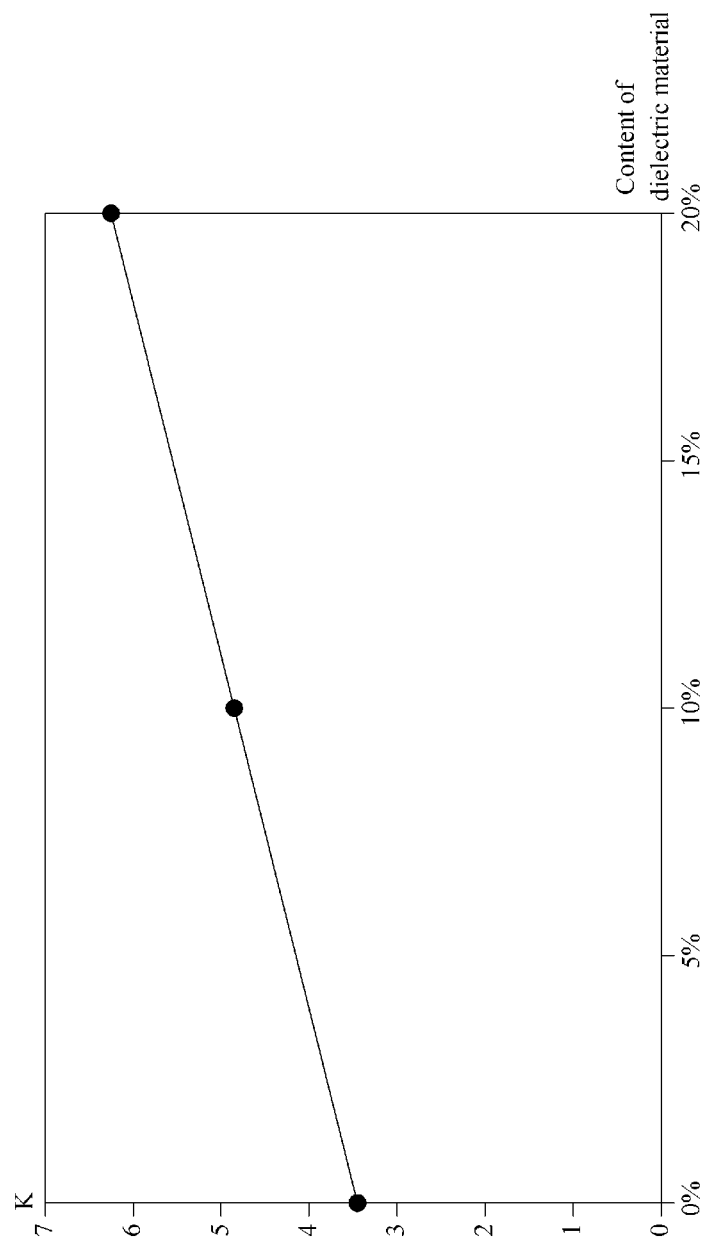
FIG. 7 shows a schematic plot of variations of capacitance with respect to different contents of the dielectric material for the preferred embodiment of the stretch sensor in accordance with the present invention.

Referring continuously to FIG. 7, a schematic plot of variations of dielectric constant with respect to different contents of the dielectric material for the preferred embodiment of the stretch sensor in accordance with the present invention is shown. At x=0.9 for the dielectric material ($Sr_{1-x}Ca_xTiO_3$ compound), the corresponding dielectric material ($Sr_{0.1}Ca_{0.9}TiO_3$ compound) would have a dielectric constant of 15.65. Namely, in the case that the content of the dielectric material in the elastic resin is 10 wt %, the dielectric constant (K value) of the elastic dielectric layer 3 would be 4.85 F/m. While the content of the dielectric material in the elastic resin is 20 wt %, the dielectric constant (K value) of the elastic dielectric layer 3 would be 6.25 F/m. Further, while the content of the dielectric material in the elastic resin is reduced to none, the dielectric constant (K value) of the elastic dielectric layer 3 would be 36.45 F/m, which is equal to the dielectric constant of the elastic resin itself. Thereupon, by adding 10-20 wt % dielectric material into the elastic dielectric layer 3, the entire equivalent dielectric constant of the elastic dielectric layer 3 would be effectively raised.

Figure 8:
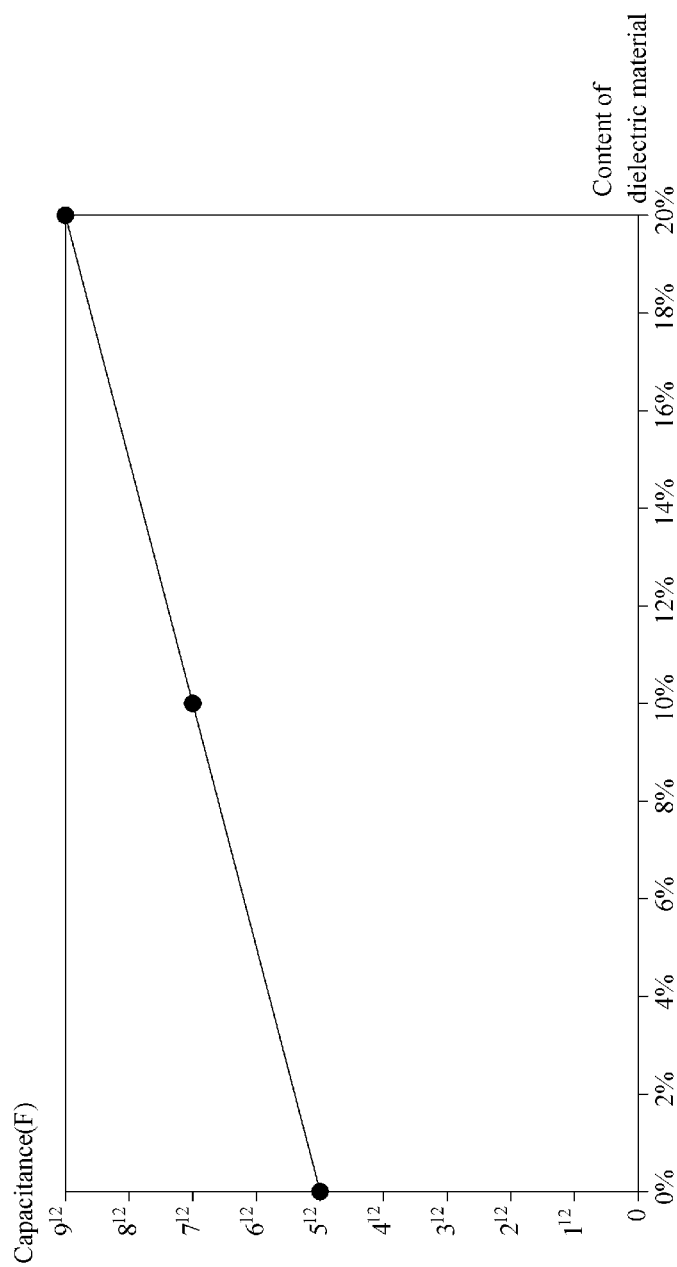
FIG. 8 shows another schematic plot of variations of capacitance with respect to different contents of the dielectric material for the preferred embodiment of the stretch sensor in accordance with the present invention.

Referring continuously to FIG. 8, another schematic plot of variations of capacitance with respect to different contents of the dielectric material for the preferred embodiment of the stretch sensor in accordance with the present invention is shown. Similarly, by having the x=0.9 dielectric material ($Sr_{0.1}Ca_{0.9}TiO_3$ compound) as an example, the capacitance (F) of the elastic dielectric layer 3 added by the dielectric material would vary for $5^{-12}$ at 0 wt % dielectric material, $7^{-12}$ at 10 wt % dielectric material, and $9^{-12}$ at 20 wt % dielectric material.

Figure 9:
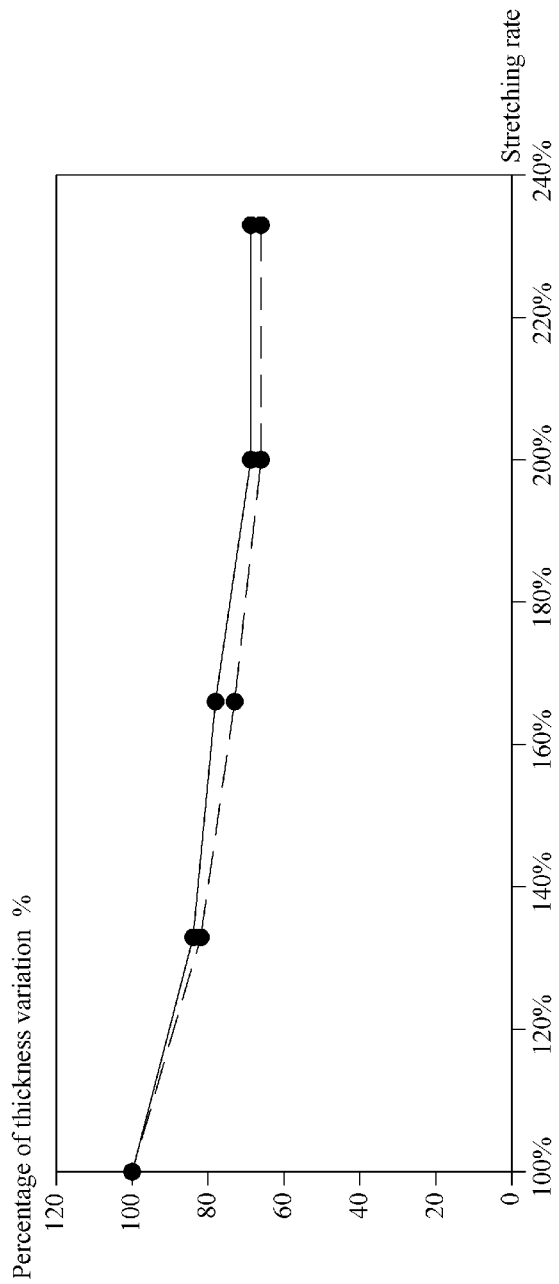
FIG. 9 shows a schematic plot of percentages of thickness variation with respect to different stretching rates of the elastic dielectric layer for the preferred embodiment of the stretch sensor in accordance with the present invention.

Referring continuously to FIG. 9, a schematic plot of percentages of thickness variation with respect to different stretching rates of the elastic dielectric layer for the preferred embodiment of the stretch sensor in accordance with the present invention is shown. Similarly, by having the x=0.9 dielectric material ($Sr_{0.1}Ca_{0.9}TiO_3$ compound) as an example, while the elastic dielectric layer 3 is stretched to have an about 235% stretching rate, both the dashed-line curve for the elastic dielectric layer 3 added by 10 wt % dielectric material and the the solid-line curve for the elastic dielectric layer 3 added by 20 wt % dielectric material present a linear descending trend.

In summary, by adding 10-20 wt % dielectric material ($Sr_{1-x}Ca_xTiO_3$ compound, $Sr_{1-y}Ba_yTiO_3$ compound or $BaTiO_3$ compound, with $0.1 \le x \le 0.9$ and $0.1 \le y \le 0.9$) to the elastic dielectric layer of the stretch sensor in accordance with the present invention, the entire equivalent dielectric constant of the elastic dielectric layer can be effectively controlled within 4.85-408.31 F/m. In comparison with the elastic resin in the art that provides a 2-4 dielectric constant after an expensive material modification, the dielectric constant of the elastic dielectric layer can be raised by adding the dielectric material, and thereby the capacitance of the elastic dielectric layer can be increased as well. Thereupon, the manufacturing cost thereof would be reduced substantially.

While the present invention has been particularly shown and described with reference to a preferred embodiment, it will be understood by those skilled in the art that various changes in form and detail may be without departing from the spirit and scope of the present invention.

What is claimed is:

1. A stretch sensor, comprising:
   a first elastic insulating layer, including an elastic resin;
   a first elastic conductive layer, disposed on the first elastic insulating layer, and including the elastic resin and a conductive material;
   an elastic dielectric layer, disposed on the first elastic conductive layer, including the elastic resin and a dielectric material, the dielectric material being composed by at least one of an $Sr_{1-x}Ca_xTiO_3$ compound, an $Sr_{1-y}Ba_yTiO_3$ compound and a $BaTiO_3$ compound with $0.1 \le x \le 0.9$ and $0.1 \le y \le 0.9$, so as to have a dielectric constant (K value) of the dielectric material within 5.65-2087.3 F/m;
   a second elastic conductive layer, disposed on the elastic dielectric layer, including the elastic resin and the conductive material; and
   a second elastic insulating layer, disposed on the second elastic conductive layer, including the elastic resin;
   wherein the dielectric constant of the elastic dielectric layer is within 4.85-408.31 F/m;
   wherein constituents of the elastic resin includes at least a mono vinyl terminated polydimethylsiloxane, a vinyl modified Q silica resin and a polydimethylhydrogensiloxane (Methylhydrosiloxane-dimethylsiloxane copolymer, trimethylsiloxane terminated); and wherein a content of the mono vinyl terminated polydimethylsiloxane in the elastic resin is larger than 70 wt %.

2. The stretch sensor of claim 1, wherein the elastic dielectric layer includes 10-20 wt % the dielectric material, and the dielectric material including the $Sr_{1-x}Ca_xTiO_3$ compound has the dielectric constant within 15.65-31.31 F/m so as to have the dielectric constant of the elastic dielectric layer within 4.85-9.45 F/m.

3. The stretch sensor of claim 1, wherein the elastic dielectric layer includes 10-20 wt % the dielectric material, and the dielectric material including the $Sr_{1-y}Ba_yTiO_3$ compound has the dielectric constant within 139.84-206.64 F/m so as to have the dielectric constant of the elastic dielectric layer within 18.66-44.63 F/m.

4. The stretch sensor of claim 1, wherein the elastic dielectric layer includes 10-20 wt % the dielectric material, and the dielectric material including the $BaTiO_3$ compound has the dielectric constant of 2087.3 F/m so as to have the dielectric constant of the elastic dielectric layer within 207.48-408.31 F/m.

5. A stretch sensor, comprising:
a first elastic insulating layer, including an elastic resin;
a first elastic conductive layer, disposed on the first elastic insulating layer, and including the elastic resin and a conductive material;
an elastic dielectric layer, disposed on the first elastic conductive layer, including the elastic resin and a dielectric material, the dielectric material being composed by at least one of an Sr1−xCaxTiO3 compound, an Sr1−yBayTiO3 compound and a BaTiO3 compound with 0.1≤x≤0.9 and 0.1≤y≤0.9, so as to have a dielectric constant (K value) of the dielectric material within 5.65-2087.3 F/m;
a second elastic conductive layer, disposed on the elastic dielectric layer, including the elastic resin and the conductive material; and
a second elastic insulating layer, disposed on the second elastic conductive layer, including the elastic resin;
wherein the dielectric constant of the elastic dielectric layer is within 4.85-408.31 F/m;
wherein constituents of the elastic resin includes at least a mono vinyl terminated polydimethylsiloxane, a vinyl modified Q silica resin and a polydimethylhydrogensiloxane (Methylhydrosiloxane-dimethylsiloxane copolymer, trimethylsiloxane terminated); and
wherein a content of the vinyl modified Q silica resin in the elastic resin is less than 30 wt %.

6. The stretch sensor of claim 5, wherein the elastic dielectric layer includes 10-20 wt % the dielectric material, and the dielectric material including the $Sr_{1-x}Ca_xTiO_3$ compound has the dielectric constant within 15.65-31.31 F/m so as to have the dielectric constant of the elastic dielectric layer within 4.85-9.45 F/m.

7. The stretch sensor of claim 5, wherein the elastic dielectric layer includes 10-20 wt % the dielectric material, and the dielectric material including the $Sr_{1-y}Ba_yTiO_3$ compound has the dielectric constant within 139.84-206.64 F/m so as to have the dielectric constant of the elastic dielectric layer within 18.66-44.63 F/m.

8. The stretch sensor of claim 5, wherein the elastic dielectric layer includes 10-20 wt % the dielectric material, and the dielectric material including the $BaTiO_3$ compound has the dielectric constant of 2087.3 F/m so as to have the dielectric constant of the elastic dielectric layer within 207.48-408.31 F/m.

9. A stretch sensor, comprising:
a first elastic insulating layer, including an elastic resin;
a first elastic conductive layer, disposed on the first elastic insulating layer, and including the elastic resin and a conductive material;
an elastic dielectric layer, disposed on the first elastic conductive layer, including the elastic resin and a dielectric material, the dielectric material being composed by at least one of an Sr1−xCaxTiO3 compound, an Sr1−yBayTiO3 compound and a BaTiO3 compound with 0.1≤x≤0.9 and 0.1 so as to have a dielectric constant (K value) of the dielectric material within 5.65-2087.3 F/m;
a second elastic conductive layer, disposed on the elastic dielectric layer, including the elastic resin and the conductive material; and
a second elastic insulating layer, disposed on the second elastic conductive layer, including the elastic resin;
wherein the dielectric constant of the elastic dielectric layer is within 4.85-408.31 F/m;
wherein constituents of the elastic resin includes at least a mono vinyl terminated polydimethylsiloxane, a vinyl modified Q silica resin and a polydimethylhydrogensiloxane (Methylhydrosiloxane-dimethylsiloxane copolymer, trimethylsiloxane terminated); and
wherein a content of the polydimethylhydrogensiloxane in the elastic resin is less than 10 wt %.

10. The stretch sensor of claim 9, wherein the elastic dielectric layer includes 10-20 wt % the dielectric material, and the dielectric material including the $Sr_{1-x}Ca_xTiO_3$ compound has the dielectric constant within 15.65-31.31 F/m so as to have the dielectric constant of the elastic dielectric layer within 4.85-9.45 F/m.

11. The stretch sensor of claim 9, wherein the elastic dielectric layer includes 10-20 wt % the dielectric material, and the dielectric material including the $Sr_{1-y}Ba_yTiO_3$ compound has the dielectric constant within 139.84-206.64 F/m so as to have the dielectric constant of the elastic dielectric layer within 18.66-44.63 F/m.

12. The stretch sensor of claim 9, wherein the elastic dielectric layer includes 10-20 wt % the dielectric material, and the dielectric material including the $BaTiO_3$ compound has the dielectric constant of 2087.3 F/m so as to have the dielectric constant of the elastic dielectric layer within 207.48-408.31 F/m.

* * * * *